United States Patent [19]
Chen et al.

[11] Patent Number: 6,034,252
[45] Date of Patent: Mar. 7, 2000

[54] SUBSTITUTED THIENOCYCLOALKYLPYRAZOLES: DOPAMINE RECEPTOR SUBTYPE SPECIFIC LIGANDS

[75] Inventors: Xi Chen, Killingworth; Jan W. F. Wasley, Guilford, both of Conn.

[73] Assignee: Neurogen Corporation, Branford, Conn.

[21] Appl. No.: 09/328,170

[22] Filed: Jun. 8, 1999

Related U.S. Application Data

[60] Provisional application No. 60/088,640, Jun. 9, 1998.
[51] Int. Cl.[7] .................................................. C07D 495/04
[52] U.S. Cl. ......................................................... 548/359.5
[58] Field of Search .......................................... 548/359.5

[56] References Cited

PUBLICATIONS

Prim et al, Chemical Abstracts, vol. 124, No. 289154; CA Index Guide or Ring System Handbook, 1996.

*Primary Examiner*—Robert W. Ramsuer
*Attorney, Agent, or Firm*—McDonnell Boehnen Hulbert & Berghoff; Steven J. Sarussi

[57] ABSTRACT

Disclosed are compounds of the formula:

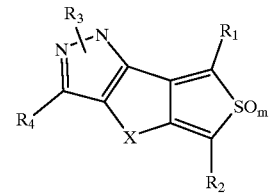

or the pharmaceutically acceptable salts thereof wherein wherein:

$R_1$, $R_2$, and and $R_4$ independenlty represent hydrogen, halogen, alkyl, cyano, alkoxycarbonyl, trifluoromethoxy, $SO_2NH_2$ or trifluoromethyl;

$R_3$ represents hydrogen, halogen, alkyl, alkoxy, alkylthio, hydroxy, amino, mono- or di($C_1$–$C_6$)alkylamino, cyano, alkoxycarbonyl, trifluoromethoxy, $SO_2NH_2$ or trifluoromethyl; or $R_3$ represents optionally substituted phenyl;

X represents $(CH_2)_n$ where n is an integer; and m is 0 or an integer, which compounds are useful for the treatment and/or prevention of neuropsychological disorders including, but not limited to, schizophrenia, mania, dementia, depression, anxiety, compulsive behavior, substance abuse, Parkinson-like motor disorders and motion disorders related to the use of neuroleptic agents.

30 Claims, No Drawings

SUBSTITUTED THIENOCYCLOALKYLPYRAZOLES: DOPAMINE RECEPTOR SUBTYPE SPECIFIC LIGANDS

This is a continuation-in-part of application Ser. No. 60/088,640 filed Jun. 9. 1998.

BACKGROUND OF THE INVENTION

1. Field of the Invention

This invention relates to substituted thienocycloalkylpyrazoles and to pharmaceutical compositions containing such compounds. It also relates to the use of such compounds in the treatment or prevention of psychotic disorders such as schizophrenia and other central nervous system diseases.

2. Description of the Related Art

The therapeutic effect of conventional antipsychotics, known as neuroleptics, is generally believed to be exerted through blockade of dopamine receptors. However, neuroleptics are frequently responsible for undesirable extrapyramidal side effects (EPS) and tardive dyskinesias, which are attributed to blockade of $D_2$ receptors in the striatal region of the brain. The dopamine $D_4$ receptor subtype has been identified (Nature, 347: 146 (Sokoloff et al., 1990)). Its unique localization in limbic brain areas and its differential recognition of various antipsychotics suggest that the $D_4$ receptor may play a major role in the etiology of schizophrenia. Selective $D_4$ antagonists are considered effective antipsychotics free from the neurological side effects displayed by conventional neuroleptics.

SUMMARY OF THE INVENTION

This invention provides novel compounds of Formula I which interact with dopamine receptor subtypes. Accordingly, a broad aspect of the invention is directed to a compound of Formula I:

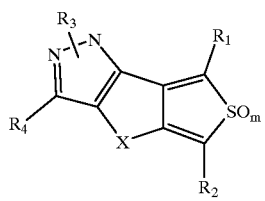

wherein:

$R_1$, $R_2$, and and $R_4$ are the same or different and represent hydrogen, halogen, $C_1$–$C_6$ alkyl, cyano, $C_1$–$C_4$ alkoxycarbonyl, trifluoromethoxy, $SO_2NH_2$ or trifluoromethyl;

$R_3$ represents hydrogen, halogen, $C_1$–$C_6$ alkyl, $C_1$–$C_6$ alkoxy, $C_1$–$C_6$ alkylthio, hydroxy, amino, mono- or di($C_1$–$C_6$)alkylamino, cyano, $C_1$–$C_4$ alkoxycarbonyl, trifluoromethoxy, $SO_2NH_2$ or trifluoromethyl; or $R_3$ represents phenyl optionally substituted with halogen, $C_1$–$C_6$ alkyl, $C_1$–$C_6$ alkoxy, $C_1$–$C_6$ alkylthio, hydroxy, amino, mono- or di($C_1$–$C_6$)alkylamino, or cyano;

X represents $(CH_2)_n$ where n is an integer of from 1 to 4; and m is 0, 1 or 2.

Dopamine $D_4$ receptors are concentrated in the limbic system (Science, 265: 1034 (Taubes, 1994)) which controls cognition and emotion. Therefore, compounds that interact with these receptors are useful in the treatment of cognitive disorders. Such disorders include cognitive deficits which are a significant component of the negative symptoms (social withdrawal and unresponsiveness) of schizophrenia. Other disorders include those involving memory impairment or attention deficit disorders.

Compounds of the present invention demonstrate high affinity and selectivity in binding to the $D_4$ receptor subtype. These compounds are therefore useful in treatment of a variety of neuropsychological disorders, such as, for example, schizophrenia, psychotic depression and mania. Other dopamine-mediated diseases such as Parkinsonism and tardive dyskinesias can also be treated directly or indirectly by modulation of $D_4$ receptors.

Compounds of this invention are also useful in the treatment of depression, memory-impairment or Alzheimer's disease by modulation of $D_4$ receptors since they exist selectively in areas known to control emotion and cognitive functions.

Thus, in another aspect, the invention provides methods for treatment and/or prevention of neuropsychochological or affective disorders including, for example, schizophrenia, mania, dementia, depression, anxiety, compulsive behavior, substance abuse, memory impairment, cognitive deficits, Parkinson-like motor disorders, e.g., Parkinsonism and dystonia, and motion disorders related to the use of neuroleptic agents. In addition, the compounds of the invention are useful in treatment of depression, memory-impairment or Alzheimer's disease. Further, the compounds of the present invention are useful for the treatment of other disorders that respond to dopaminergic blockade, e.g., substance abuse and obsessive compulsive disorder. These compounds are also useful in treating the extrapyramidal side effects associated with the use of conventional neuroleptic agents.

In yet another aspect, the invention provides pharmaceutical compositions comprising compounds of Formula I.

In another aspect, the invention provides intermediates useful in the preparation of compounds of Formulae I and II.

DETAILED DESCRIPTION OF THE INVENTION

Preferred compounds of Formula I are those where $R_1$ and $R_2$ are independently $C_1$–$C_3$ alkyl. More preferred compounds of Formula I are those wherein $R_1$ and $R_2$ are independently $C_1$–$C_3$ alkyl and $R_4$ is hydrogen or $C_1$–$C_6$ alkyl. Particularly preferred compounds of Formula I are those where $R_3$ is hydrogen, $C_1$–$C_6$ alkyl, or optionally substituted phenyl. In the most particularly preferred compounds of I, $R_3$ is hydrogen, $C_1$–$C_3$ alkyl, or unsubstituted phenyl.

When $R_3$ is phenyl, the phenyl group is preferably attached to the nitrogen atom adjacent the carbon carrying $R_4$.

Preferred compounds of the invention include those of Formula II:

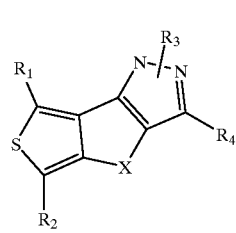

wherein:

$R_1$, $R_2$, and $R_4$ are the same or different and represent hydrogen, halogen, $C_1$–$C_6$ alkyl, cyano, $C_1$–$C_4$ alkoxycarbonyl, trifluoromethoxy, $SO_2NH_2$ or trifluoromethyl;

$R_3$ represents hydrogen, halogen, $C_1$–$C_6$ alkyl, $C_1$–$C_6$ alkoxy, $C_1$–$C_6$ alkylthio, hydroxy, amino, mono- or di($C_1$–$C_6$)alkylamino, cyano, $C_1$–$C_4$ alkoxycarbonyl, trifluoromethoxy, $SO_2NH_2$ or trifluoromethyl; or $R_3$ represents phenyl optionally substituted with halogen, $C_1$–$C_6$ alkyl, $C_1$–$C_6$ alkoxy, $C_1$–$C_6$ alkylthio, hydroxy, amino, mono- or di($C_1$–$C_6$)alkylamino, or cyano; and X represents $(CH_2)_n$ where n is an integer of from 1 to 4.

A first set of preferred compounds of Formula II are those where n is 2. Compounds where n is 2 are referred to hereinafter as Formula II-2.

Preferred compounds of Formula II-2 are those wherein $R_1$ and $R_2$ are independently $C_1$–$C_3$ alkyl. More preferred compounds of Formula II-2 are those wherein $R_1$ and $R_2$ are independently $C_1$–$C_3$ alkyl and $R_4$ is hydrogen or $C_1$–$C_6$ alkyl. Other more preferred compounds of Formula II-2 are those wherein $R_1$ and $R_2$ are independently $C_1$–$C_3$ alkyl and $R_4$ is hydrogen. Particularly preferred compounds of II-2 have $R_3$ as hydrogen, $C_1$–$C_6$ alkyl, or optionally substituted phenyl. In the most particularly preferred compounds of II-2, $R_3$ is hydrogen, $C_1$–$C_3$ alkyl, or unsubstituted phenyl.

A second set of preferred compounds of Formula II are those where n is 3. Compounds where n is 3 are referred to hereinafter as Formula II-3.

Preferred compounds of Formula II-3 are those wherein $R_1$ and $R_2$ are independently $C_1$–$C_3$ alkyl. More preferred compounds of Formula II-3 are those wherein $R_1$ and $R_2$ are independently $C_1$–$C_3$ alkyl and $R_4$ is hydrogen or $C_1$–$C_6$ alkyl. Other more preferred compounds of Formula II-3 are those wherein $R_1$ and $R_2$ are independently $C_1$–$C_3$ alkyl and $R_4$ is hydrogen. Particularly preferred compounds of II-3 have $R_3$ as hydrogen, $C_1$–$C_6$ alkyl, or optionally substituted phenyl. In the most particularly preferred compounds of II-3, $R_3$ is hydrogen, $C_1$–$C_3$ alkyl, or unsubstituted phenyl.

A third set of preferred compounds of Formula II are those where n is 4. Compounds where n is 3 are referred to hereinafter as Formula II-4.

Preferred compounds of Formula II-4 are those wherein $R_1$ and $R_2$ are independently $C_1$–$C_3$ alkyl. More preferred compounds of Formula II-4 are those wherein $R_1$ and $R_2$ are independently $C_1$–$C_3$ alkyl and $R_4$ is hydrogen or $C_1$–$C_6$ alkyl. Other more preferred compounds of Formula II-4 are those wherein $R_1$ and $R_2$ are independently $C_1$–$C_3$ alkyl and $R_4$ is hydrogen. Particularly preferred compounds of II-4 have $R_3$ as hydrogen, $C_1$–$C_6$ alkyl, or optionally substituted phenyl. In the most particularly preferred compounds of II-4, $R_3$ is hydrogen, $C_1$–$C_3$ alkyl, or unsubstituted phenyl.

The invention also provides intermediates useful in preparing compounds of Formulae I and II. These intermediates have Formulae III–VI.

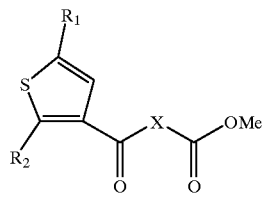

III where $R_1$, $R_2$, and X are defined as above for Formula I; and $R_5$ is hydrogen or $C_1$–$C_6$ alkyl.

Preferred intermediate compounds of Formula III are those where X is ethylene or propylene; $R_1$ and $R_2$ are independently $C_1$–$C_6$ alkyl; and $R_5$ is $C_1$–$C_6$ alkyl, preferably methyl.

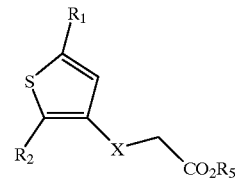

IV where $R_1$, $R_2$, and X are defined as above for Formula I; and $R_5$ is hydrogen or $C_1$–$C_6$ alkyl.

Preferred intermediate compounds of Formula IV are those where X is ethylene or propylene; $R_1$ and $R_2$ are independently $C_1$–$C_6$ alkyl; and $R_5$ is hydrogen.

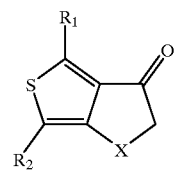

V where $R_1$, $R_2$, and X are defined as above for Formula I.

Preferred intermediate compounds of Formula V are those where X is ethylene or propylene; $R_1$ and R2 are independently $C_1$–$C_6$ alkyl.

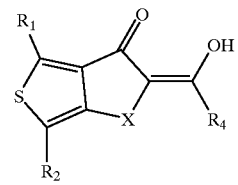

VI where $R_1$, $R_2$, and X, and $R_4$ are defined as above for Formula I.

Preferred intermediate compounds of Formula VI are those where X is ethylene or propylene; $R_1$ and $R_2$ are independently $C_1$–$C_6$ alkyl; and $R_4$ hydrogen.

In certain situations, the compounds of Formula I may contain one or more asymmetric carbon atoms, so that the compounds can exist in different stereoisomeric forms. These compounds can be, for example, racemates or optically active forms. In these situations, the single enantiomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral HPLC column.

Representative compounds of the present invention, which are encompassed by Formula I, include, but are not limited to the compounds in Table I and their pharmaceutically acceptable acid addition salts. In addition, if the compound of the invention is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds.

Non-toxic pharmaceutical salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, HOOC—(CH$_2$)$_n$—COOH where n is 0–4, and the like. Those skilled in the art will recognize a wide variety of non-toxic pharmaceutically acceptable addition salts.

The present invention also encompasses the acylated prodrugs of the compounds of Formula I. Those skilled in the art will recognize various synthetic methodologies which may be employed to prepare non-toxic pharmaceutically acceptable addition salts and acylated prodrugs of the compounds encompassed by Formula I.

Where a compound exists in various tautomeric forms, the invention is not limited to any one of the specific tautomers. The invention includes all tautomeric forms of a compound.

By "C$_1$–C$_6$ alkyl" or "lower alkyl" in the present invention is meant straight or branched chain alkyl groups having 1–6 carbon atoms, such as, for example, methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl. Preferred C$_1$–C$_6$ alkyl groups are methyl, ethyl, propyl, butyl, cyclopropyl and cyclopropylmethyl.

By "C$_1$–C$_6$ alkoxy" or "lower alkoxy" in the present invention is meant straight or branched chain alkoxy groups having 1–6 carbon atoms, such as, for example, methoxy, ethoxy, propoxy, isopropoxy, n-butoxy, sec-butoxy, tert-butoxy, pentoxy, 2-pentyl, isopentoxy, neopentoxy, hexoxy, 2-hexoxy, 3-hexoxy, and 3-methylpentoxy.

By the term "halogen" in the present invention is meant fluorine, bromine, chlorine, and iodine.

Compounds including the following structure

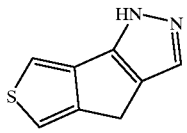

hydropyrazolo[5',4'-4,3]cyclopenta[2,1-c]thiophenes.

Compounds including the following structure

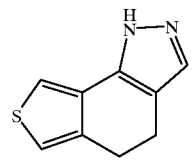

dihydrothiopheno[3,4-g]1 H-indazoles.

Compounds including the following structure

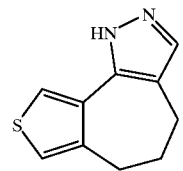

4,5,6-trihydropyrazolo[5',4'-4,3]cyclohepta[2,1-c] thiophenes.

Representative thienocycloalkylpyrazoles of the present invention are shown in Table 1. The number below each compound is its compound number.

TABLE 1

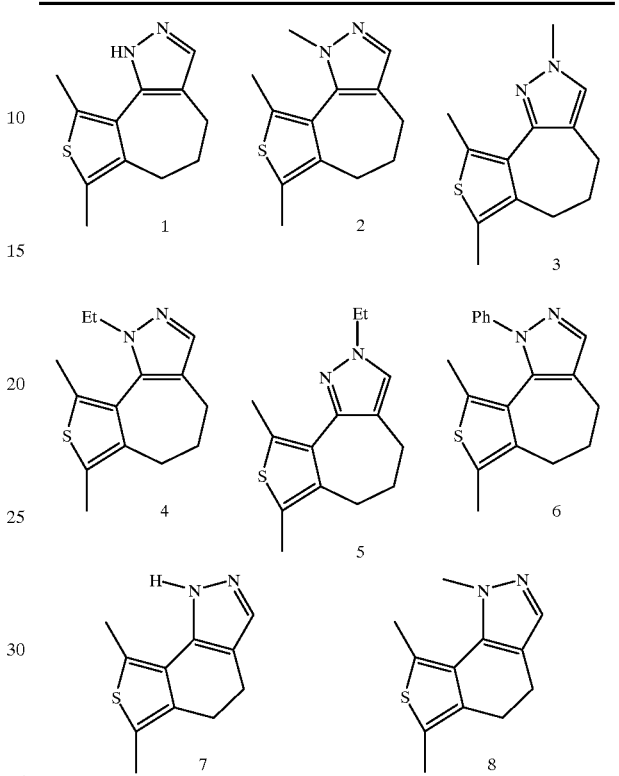

The invention also pertains to the use of compounds of general Formula I in the treatment of neuropsychological disorders. The selective interaction of compounds of the invention with dopamine receptors results in the pharmacological activity of these compounds.

The compounds of general formula I may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition, there is provided a pharmaceutical formulation comprising a compound of general formula I and a pharmaceutically acceptable carrier. One or more compounds of general formula I may be present in association with one or more non-toxic pharmaceutically acceptable carriers and/or diluents and/or adjuvants and if desired other active ingredients. The pharmaceutical compositions containing compounds of general formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

The compounds of general formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compounds of general formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

A representative synthesis of the thienocycloheptapyrazoles of the invention is presented in Scheme I.

Scheme 1

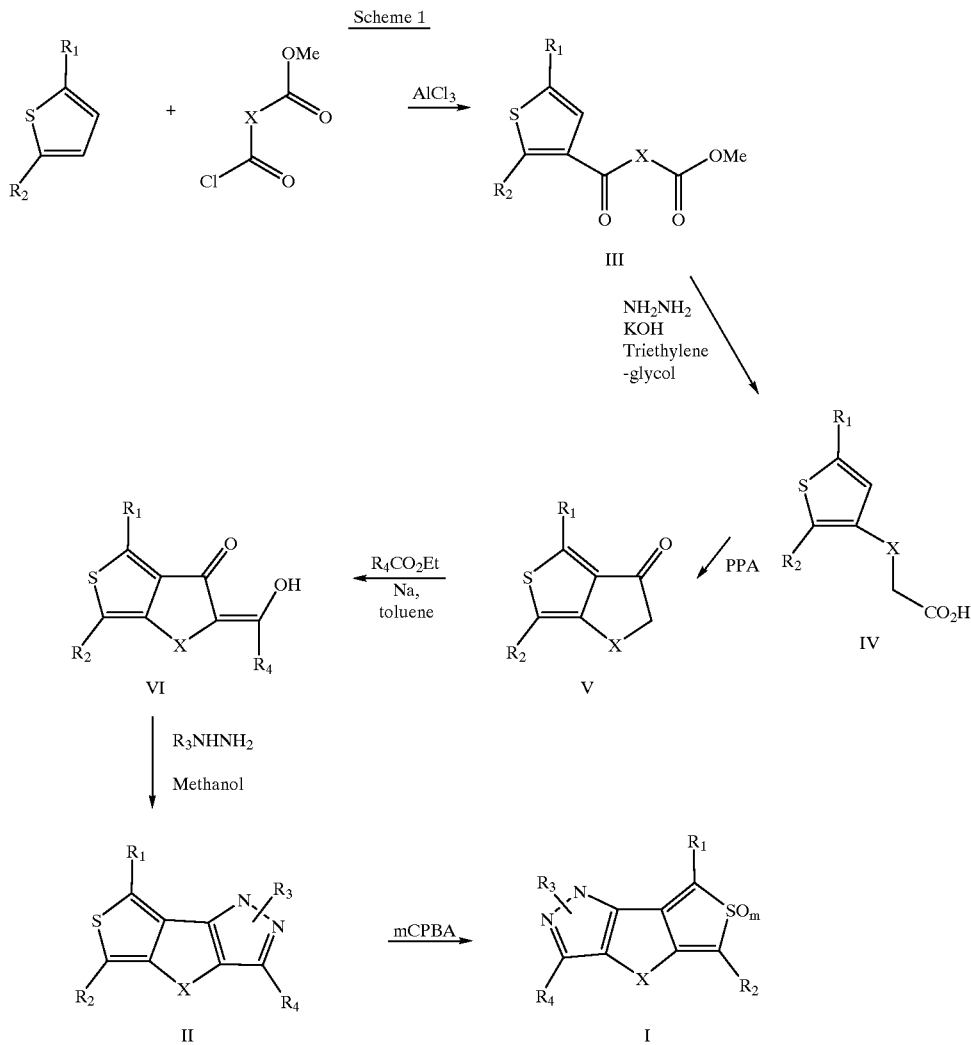

wherein $R_1$, $R_2$, $R_3$, $R_4$ and X are as defined above for Formula 1.

As shown, a 2,5-disubstituted thiophene may be condensed with an acidchloride in a Friedel-Crafts acylation to provide a 3-acylthiophene of general structure III. Acylthiophene III may then be reduced using appropriate conditions, e.g., Wolf-Kishner conditions, to provide thien-3-ylalkylcarboxylic acid IV. Acid IV can then be converted to cycloalkylthiophenone V using polyphosphoric acid, generally with heating at, for example, about 125–150° C. Further acylation of V at the position alpha to the carbonyl with a suitable ester in a solvent such as toluene provides compound VI. Such transformation may be achieved using an alkali metal such as sodium or potassium to form an anion at the alpha position. A substituted hydrazine may then be exploited to form the pyrazole ring and yield thienocycloalkylpyrazole II. Further oxidation using m-chloroperoxybenzoic acid will furnish compounds of Formula I. Those having skill in the art will recognize that the starting materials may be varied and/or additional steps employed to produce compounds encompassed by the present invention. For example, in certain situations, protection of reactive groups may be necessary to achieve a specific transformation.

The disclosures of all articles and references mentioned in this application, including patents, are incorporated herein by reference.

The preparation of the compounds of the present invention is illustrated further by the following examples which are not to be construed as limiting the invention in scope or spirit to the specific procedures and compounds described in them.

The starting materials and various intermediates may be obtained from commercial sources, prepared from commercially available organic compounds, or prepared using well-known synthetic methods.

EXAMPLE 1

1. 5-(2,5-Dimethyl-3-thiophenyl)pentanoic acid 2,5-Dimethylthiophene (8 g, 71.4 mmol) and methyl chloroformylbutyrate (10 g, 65.8 mmol) are dissolved in 40 mL 1,2-dichloroethane. The reaction mixture is then cooled to −10° C. $AlCl_3$ was added in portion in 15 min. The resulting mixture is stirred at 0° C. for another 1 hr., poured into ice and concentrated HCl (3:1), and extracted with dichloromethane. The organic layer is washed with 10% HCl, water and 5% sodium bicarbonate. It is then dried over sodium sulfate and the solvent evaporated under reduced pressure. The resulting yellow oil is redissolved in 60 mL triethyleneglycol with 20 mL 80% hydrazine and 20 g KOH. The reaction mixture is then heated to 140° C. for 10 min. and then to 180° C. to distill off the remaining hydrazine and water. The mixture is maintained at 205° C. overnight. After the reaction is cooled to room temperature, it is diluted with water, acidified with conc. HCl and extrated with ether. The ether layer is washed exaustively with water and dried over sodium sulfate. Evaporation of the solvent under reduced pressure yields 5-(2,5-dimethyl-3-thiophenyl)pentanoic acid as a brown oil (12 g, 86%) $^1$H NMR (CDCl$_3$) 6.45 (s, 1 H), 2.50–2.10 (m, 10 H), 1.83–1.55 (m, 4 H).

2. 1,3-Dimethyl-5,6,7,8-tetrahydro-4 H-cyclohepta[1,2-c]-thiophen-4-one 5-(2,5-Dimethyl-3-thiophenyl)pentanoic acid (12 g, 56.6 mmol) is heated in 30 g of polyphosphoric acid at 140° C. for 2 hr. After the reaction mixture is cooled to room temperature, water is added to dissolve the residual PPA. The mixture is then extracted with ether and the ether layer is washed with water, aqueous NaOH and again with water. The ether layer is then dried over sodium sulfate and the solvent evaporated under reduced pressure to yield 1,3-dimethyl-5,6,7,8-tetrahydro-4 H-cyclohepta[1,2-c]thiophen-4-one as a dark oil (8 g, 73%). $^1$H NMR (CDCl$_3$) 2.70 (t, J=6.0 Hz, 2 H), 2.64 (dd, J=5.0, 7.0 Hz, 2 H), 2.55 (s, 3 H), 2.28 (s, 3 H), 1.79 (m, 4 H).

3. 7,9-Dimethyl-1,4,5,6-tetrahydrothieno[3',4':6,7]-cyclohepa [1,2-c]pyrazole

Ethyl formate (229 mg, 8.3 mmol) and sodium (230 mg, 10.0 mmol) are stirred in 20 mL toluene. 4 H-1,3-dimethyl-5,6,7,8-tetrahydrocycloheptathiophene-4-one (1 g, 5.2 mmol) in 10 mL toluene are then added dropwise to the reaction mixture which is subsequently heated at 60° C. overnight. The reaction mixture was decanted to discard any remaining sodium and then extracted with water. The aqueous layer is washed with ether, acidified with conc. HCl, and extracted with dichloromethane. The combined organic extract is dried over sodium sulfate and the solvent evaporated under reduced pressure to yielded crude 1,3-Dimethyl-4-oxo-5,6,7,8-tetrahydro-4 H-cyclohepta[1,2-c]thiophene-5-carbaldehyde as a dark oil. The oil is redissolved in 10 mL methanol and hydrazine monohydrate (260 mg, 5.2 mmol) is added. The resulting mixture is stirred at room temperature for 1 hr. After evaporation of methanol, the resulting oil is partitioned between dichloromethane and aqueous NaOH. The organic layer is column chromatographed (20:1, dichloromethane: methanol) to afford 7,9-dimethyl-1,4,5,6-tetrahydrothieno[3',4':6,7]cyclo-hepta[1,2-c]pyrazole (Compound 1) as a yellow solid (0.5 g, 44%) $^1$H NMR (CDCl$_3$) 7.42 (s, 1 H), 2.74 (t, J=7.0 Hz, 2 H), 2.60–2.57 (m, 5 H), 2.32 (s, 3 H), 1.93 (m, 4 H). The hydrochloride salt is crystalized from ether (m.p. 178–180° C.).

EXAMPLE 2

The following compounds are prepared essentially according to the procedures set forth above in Example 1:

(a) 1,7,9-Trimethyl-1,4,5,6-tetrahydrothieno[3',4':6,7] cyclohepta[1,2-c]pyrazole hydrochloride (Compound 2, m.p. 140–142° C.)

(b) 2,7,9-Trimethyl-1,4,5,6-tetrahydrothieno[3',4':6,7] cyclohepta[1,2-c]pyrazole hydrochloride (Compound 3, m.p. 143–145° C.)

(c) 1-Ethyl-7,9-trimethyl-1,4,5,6-tetrahydrothieno[3',4':6,7] cyclohepta[1,2-c]pyrazole hydrochloride (Compound 4, m.p. 122–124° C.)

(d) 2-Ethyl-7,9-trimethyl-1,4,5,6-tetrahydrothieno[3',4':6,7] cyclohepta[1,2-c]pyrazole hydrochloride (Compound 5, m.p. 132–134° C.)

(e) 1-Phenyl-7,9-trimethyl-1,4,5,6-tetrahydrothieno[3',4':6,7]cyclohepta[1,2-c]pyrazole hydrochloride (Compound 6, m.p. 128–130° C.)

(f) 6,8-Dimethyl-1 H-4,5-dihydrothieno[3',4':5,6]cyclohexa [1,2-c]pyrazole hydrochloride (Compound 7, m.p. 220° C. dec.)

(g) 1,6,8-Timethyl-1 H-4,5-dihydrothieno[3',4':5,6] cyclohexa[1,2-c]pyrazole hydrochloride (Compound 8, m.p. 155–157° C.)

EXAMPLE 3

Assay for D$_2$ and D$_4$ Receptor Binding Activity

The utility of compounds of this invention is indicated by the assays for dopamine receptor subtype affinity described below.

Pellets of COS cells containing recombinantly produced D$_2$ or D$_4$ receptors from African Green monkey are used for the assays. The sample is homogenized in 100 volumes (w/vol) of 0.05 M Tris HCl buffer at 4° C. and pH 7.4. The sample is then centrifuged at 30,000×g and resuspended and rehomogenized. The sample is then centrifuged as described above and the final tissue sample is frozen until use. The tissue is resuspended 1:20 (wt/vol) in 0.05 M Tris HCl buffer containing 100 mM NaCl.

Incubations are carried out at 48° C. and contain 0.4 ml of tissue sample, 0.5 nM $^3$H—YM 09151-2 and the compound of interest in a total incubation of 1.0 ml. Nonspecific binding is defined as that binding found in the presence of 1 mM spiperone; without further additions, nonspecific binding is less than 20% of total binding.

The compounds of the invention exhibit Ki's of less than 1 μm on D$_4$ subtype. The compounds of the invention are generally at least about 5 time more selective for the D$_4$ receptor than the D$_2$ receptor.

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A compound of the formula:

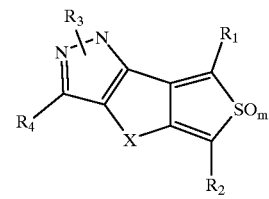

or pharmaceutically acceptable addition salts thereof wherein:

R$_1$, R$_2$, and and R$_4$ are the same or different and represent hydrogen, halogen, C$_1$–C$_6$ alkyl, cyano, C$_1$–C$_4$ alkoxycarbonyl, trifluoromethoxy, SO$_2$NH$_2$ or trifluoromethyl;

R$_3$ represents hydrogen, halogen, C$_1$–C$_6$ alkyl, C$_1$–C$_6$ alkoxy, C$_1$–C$_6$ alkylthio, hydroxy, amino, mono- or di(C$_1$–C$_6$)alkylamino, cyano, C$_1$–C$_4$ alkoxycarbonyl, trifluoromethoxy, SO$_2$NH$_2$ or trifluoromethyl; or R$_3$ represents phenyl optionally substituted with halogen, C$_1$–C$_6$ alkyl, C$_1$–C$_6$ alkoxy, C$_1$–C$_6$ alkylthio, hydroxy, amino, mono- or di(C$_1$–C$_6$)alkylamino, or cyano;

X represents $(CH_2)_n$ where n is an integer of from 1 to 4; and m is 0, 1 or 2.

2. A compound according to claim 1, wherein m is zero.
3. A compound according to claim 2, wherein n is 2.
4. A compound according to claim 3, wherein $R_1$ and $R_2$ are independently $C_1$–$C_3$ alkyl.
5. A compound according to claim 4, wherein $R_4$ is hydrogen or $C_1$–$C_6$ alkyl.
6. A compound according to claim 4, wherein $R_4$ is hydrogen.
7. A compound according to claim 6, wherein $R_3$ is hydrogen, $C_1$–$C_6$ alkyl, or optionally substituted phenyl.
8. A compound according to claim 6, wherein $R_3$ is hydrogen, $C_1$–$C_3$ alkyl, or unsubstituted phenyl.
9. A compound according to claim 2, wherein n is 3.
10. A compound according to claim 9, wherein $R_1$ and $R_2$ are independently $C_1$–$C_3$ alkyl.
11. A compound according to claim 10, wherein $R_4$ is hydrogen or $C_1$–$C_6$ alkyl.
12. A compound according to claim 10, wherein $R_4$ is hydrogen.
13. A compound according to claim 12, wherein $R_3$ is hydrogen, $C_1$–$C_6$ alkyl, or optionally substituted phenyl.
14. A compound according to claim 12, wherein $R_3$ is hydrogen, $C_1$–$C_3$ alkyl, or unsubstituted phenyl.
15. A compound according to claim 1, which is 7,9-dimethyl-1,4,5,6-tetrahydrothieno[3',4':6,7]cyclohepta[1,2-c]pyrazole hydrochloride.
16. A compound according to claim 1, which is 1,7,9-trimethyl-1,4,5,6-tetrahydrothieno[3',4':6,7]cyclohepta[1,2-c]pyrazole hydrochloride.
17. A compound according to claim 1, which is 2,7,9-trimethyl-1,4,5,6-tetrahydrothieno[3',4':6,7]cyclohepta[1,2-c]pyrazole hydrochloride.
18. A compound according to claim 1, which is 1-ethyl-7,9-trimethyl-1,4,5,6-tetrahydrothieno[3',4':6,7]cyclohepta[1,2-c]pyrazole hydrochloride.
19. A compound according to claim 1, which is 2-ethyl-7,9-trimethyl-1,4,5,6-tetrahydrothieno[3',4':6,7]cyclohepta[1,2-c]pyrazole hydrochloride.
20. A compound according to claim 1, which is 1-phenyl-7,9-trimethyl-1,4,5,6-tetrahydrothieno[3',4':6,7]cyclohepta[1,2-c]pyrazole hydrochloride.
21. A compound according to claim 1, which is 6,8-dimethyl-1,4,5-trihydrothieno[3',4':5,6]cyclohexa[1,2-c]pyrazole hydrochloride.
22. A compound according to claim 1, which is 1,6,8-trimethyl-1,4,5-trihydrothieno[3',4':5,6]cyclohexa[1,2-c]pyrazole hydrochloride.
23. A compound according to claim 1, which is 7,9-dimethyl-1,4,5,6-tetrahydrothieno[3',4':6,7]cyclohepta[1,2-c]pyrazole.
24. A compound according to claim 1, which is 1,7,9-trimethyl-1,4,5,6-tetrahydrothieno[3',4':6,7]cyclohepta[1,2-c]pyrazole.
25. A compound according to claim 1, which is 2,7,9-trimethyl-1,4,5,6-tetrahydrothieno[3',4':6,7]cyclohepta[1,2-c]pyrazole.
26. A compound according to claim 1, which is 1-ethyl-7,9-trimethyl-1,4,5,6-tetrahydrothieno[3',4':6,7]cyclohepta[1,2-c]pyrazole.
27. A compound according to claim 1, which is 2-ethyl-7,9-trimethyl-1,4,5,6-tetrahydrothieno[3',4':6,7]cyclohepta[1,2-c]pyrazole.
28. A compound according to claim 1, which is 1-phenyl-7,9-trimethyl-1,4,5,6-tetrahydrothieno[3',4':6,7]cyclohepta[1,2-c]pyrazole.
29. A compound according to claim 1, which is 6,8-dimethyl-1,4,5-trihydrothieno[3',4':5,6]cyclohexa[1,2-c]pyrazole.
30. A compound according to claim 1, which is 1,6,8-trimethyl-1,4,5-trihydrothieno[3',4':5,6]cyclohexa[1,2-c]pyrazole.

* * * * *